(12) United States Patent
Akbarnia et al.

(10) Patent No.: US 9,931,140 B2
(45) Date of Patent: Apr. 3, 2018

(54) MULTI-PLANAR AXIAL SPINAL ROD CONNECTOR

(71) Applicant: K2M, Leesburg, VA (US)

(72) Inventors: Behrooz Akbarnia, La Jolla, CA (US); Clint Boyd, Winchester, VA (US)

(73) Assignee: K2M, Inc., Leesburg, VA (US)

( * ) Notice: Subject to any disclaimer, the term of this patent is extended or adjusted under 35 U.S.C. 154(b) by 241 days.

(21) Appl. No.: 14/013,680

(22) Filed: Aug. 29, 2013

(65) Prior Publication Data

US 2014/0066990 A1 Mar. 6, 2014

Related U.S. Application Data

(60) Provisional application No. 61/695,237, filed on Aug. 30, 2012.

(51) Int. Cl.
*A61B 17/88* (2006.01)
*A61B 17/70* (2006.01)

(52) U.S. Cl.
CPC .................. *A61B 17/705* (2013.01)

(58) Field of Classification Search
CPC ............. A61B 17/7049; A61B 17/705; A61B 17/7043
USPC ..................... 606/250–299, 70, 71
See application file for complete search history.

(56) References Cited

U.S. PATENT DOCUMENTS

| | | | |
|---|---|---|---|
| 6,241,730 B1 | 6/2001 | Alby | |
| 7,175,622 B2 | 2/2007 | Farris | |
| 7,909,852 B2 * | 3/2011 | Boomer | A61B 17/7013 606/246 |
| 7,935,134 B2 | 5/2011 | Reglos et al. | |
| 7,942,908 B2 | 5/2011 | Sacher et al. | |
| 8,097,022 B2 | 1/2012 | Marik | |
| 8,147,519 B2 | 4/2012 | Wilcox | |
| 8,372,121 B2 | 2/2013 | Capote et al. | |
| 8,382,803 B2 | 2/2013 | Schmocker | |
| 8,475,499 B2 | 7/2013 | Cournoyer et al. | |
| 2003/0050640 A1 * | 3/2003 | Lee et al. | 606/61 |
| 2006/0229611 A1 * | 10/2006 | Avery | A61B 17/7011 606/260 |
| 2008/0234743 A1 * | 9/2008 | Marik | A61B 17/705 606/257 |
| 2009/0093847 A1 * | 4/2009 | Wilcox | A61B 17/705 606/259 |

(Continued)

OTHER PUBLICATIONS

U.S. Appl. No. 14/013,641, filed Aug. 29, 2013, Mundis et al.

*Primary Examiner* — Eduardo C Robert
*Assistant Examiner* — Tara R Carter
(74) *Attorney, Agent, or Firm* — Carter, DeLuca, Farrell & Schmidt, LLP

(57) ABSTRACT

A multi-planar axial spinal rod connector includes a first portion, a second portion, and a connector assembly. The first portion defines a longitudinal axis and defines a first passage. The first passage is sized and configured to slidably receive a first spinal rod. The second portion defines a second longitudinal axis and defines a second passage. The second longitudinal axis is different from the first longitudinal axis. The second passage is sized and configured to slidably receive a second spinal rod. The connector assembly is configured to fix the first and second portions relative to one another such that the first and second longitudinal axes define an angle relative to one another.

17 Claims, 5 Drawing Sheets

(56) References Cited

U.S. PATENT DOCUMENTS

2009/0163953 A1 6/2009 Biedermann et al.
2010/0036423 A1 2/2010 Hayes et al.
2013/0066375 A1 3/2013 Biedermann et al.

* cited by examiner

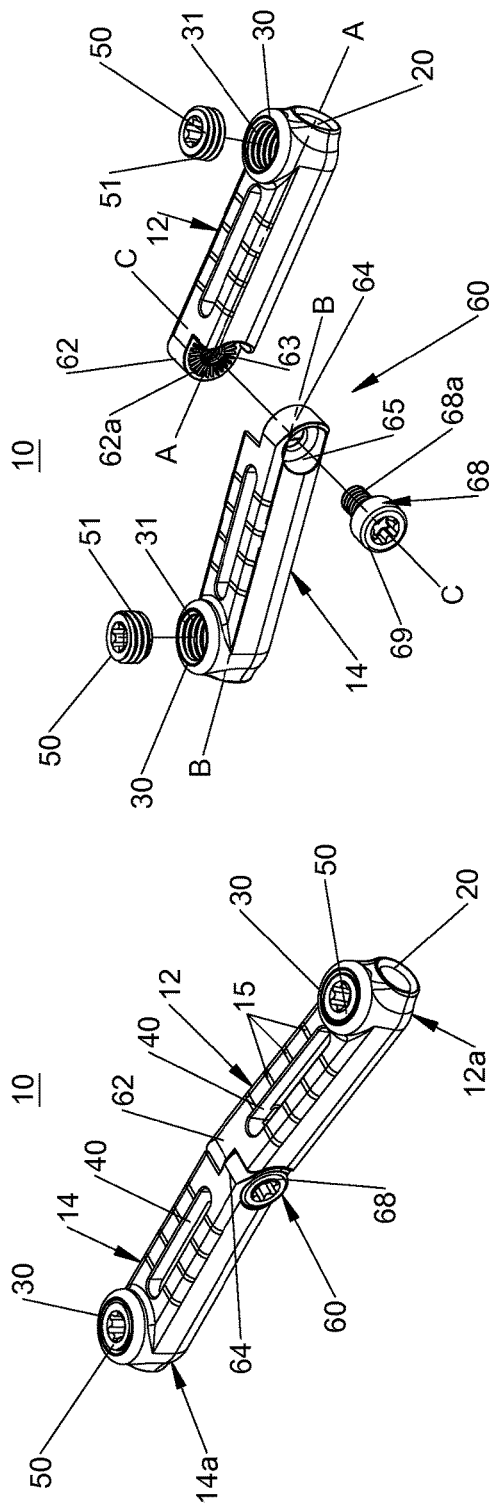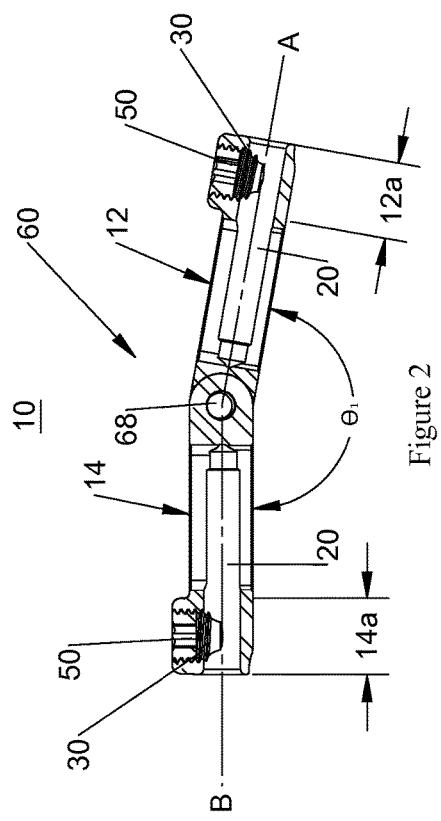
Figure 1
Figure 2
Figure 3

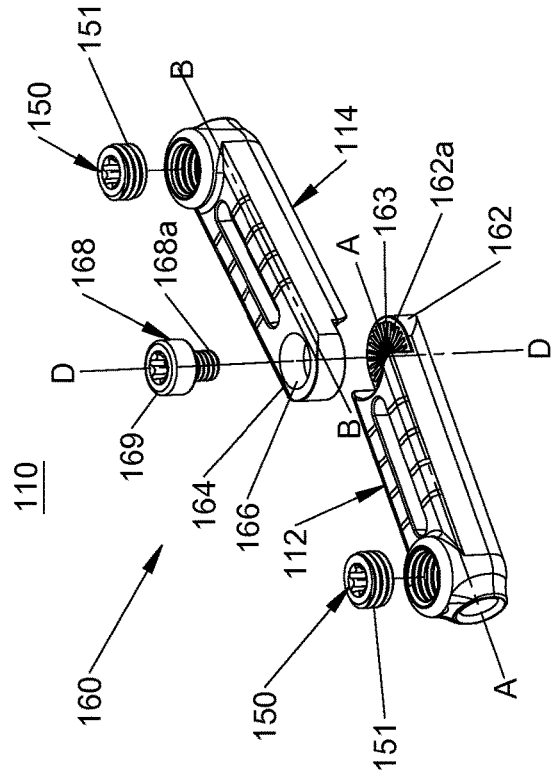
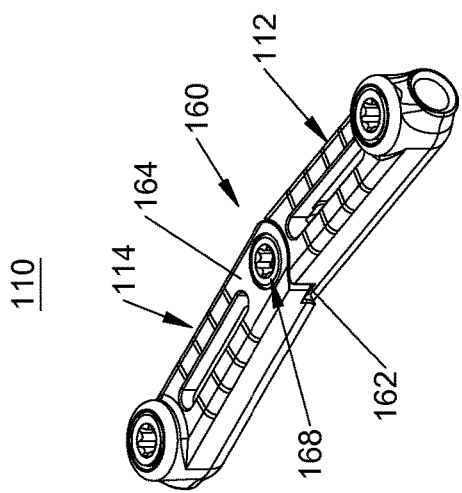
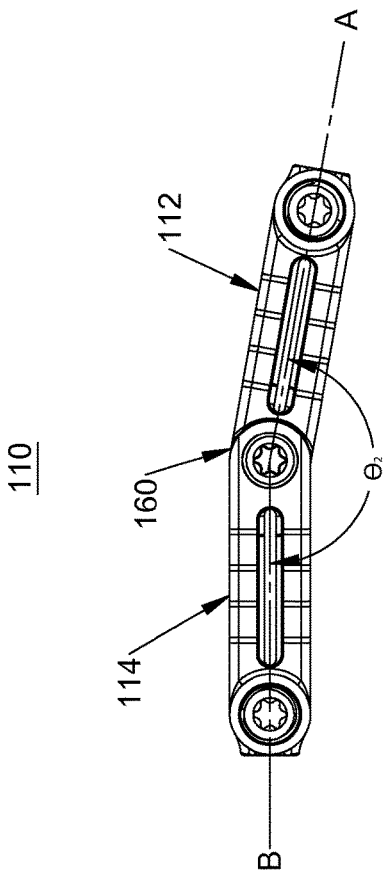

MULTI-PLANAR AXIAL SPINAL ROD CONNECTOR

CROSS-REFERENCE TO OTHER APPLICATIONS

This application claims priority to and the benefit of U.S. Provisional Application Ser. No. 61/695,237 filed Aug. 30, 2012, the disclosure of which is hereby incorporated by reference in its entirety.

BACKGROUND

1. Technical Field

The present disclosure relates to a device for use in orthopedic surgeries and, more specifically, to axial spinal rod connectors that are attachable to spinal rods in different planes relative to one another.

2. Discussion of Related Art

The human spinal column is a highly complex structure. It includes twenty-four discrete bones, known as vertebrae, coupled sequentially to one another to house and protect critical elements of the nervous system. The cervical portion of the spine, which includes the neck of the spine up to the base of the skull, includes the first seven vertebrae.

Disease, the effects of aging, or physical trauma resulting in damage to the spine has been treated in many instances by fixation or stabilization of the affected vertebra. A wide variety of spinal fixation apparatuses have been employed in surgical procedures for correcting spinal injuries and the effects of spinal diseases. Many of these apparatuses commonly use a pair of longitudinal rods running in a relatively parallel relationship to each other. Additional fixation methods are also employed that mate with the spinal rod to provide additional points of fixation. These include, but are not limited to, head to head connectors, rod to rod transverse connectors, hooks and axial rod to rod connectors.

Axial spinal rod to rod connectors are often used in subsequent surgeries when there is existing hardware already implanted in the patient. The axial spinal rod connector is used to continue the spinal rod construct from the original hardware to the new hardware that is implanted. The axial spinal rod connector provides support for the new hardware and helps to orient it appropriately with the existing hardware. In addition, an axial spinal rod connector may be used as a bridge between sections of hardware if there are two separate, non-adjacent regions that require instrumentation. Sometimes the upper thoracic region requires instrumentation as well as the lumbar region and the axial spinal rod connector may be used to connect the spinal rod from these two regions. The axial spinal rod connectors are made in various lengths, preferably 20-90 mm in length, and also may accept various spinal rod diameters, shapes and materials, for example if a smaller 4.5 mm spinal rod is used in the thoracic region and a 5.5 mm spinal rod is used in the lumbar region, the axial spinal rod connector can accommodate both of these sized spinal rods and connect with both spinal rods.

A need exists for an axial spinal rod connector to connect spinal rods in non-planar relation to one another.

SUMMARY

In aspects of the present disclosure, a multi-planar axial spinal rod connector includes a first portion, a second portion, and a connector assembly. The first portion defines a first longitudinal axis and defines a first passage sized and configured to slidably receive a first spinal rod. The second portion defines a second longitudinal axis and defines a second passage sized and configured to slidably receive a second spinal rod. The connector assembly is configured to fix the first and second portions relative to one another such that the first and second longitudinal axes define an angle relative to one another. The connector assembly may be integrally formed with the first and second portions.

In aspects of the present disclosure, the angle is adjustable. The angle may be in a range of about 45° to about 315°.

In aspects of the present disclosure, the first portion includes a first flange and the second portion includes a second flange. The first and second flanges each define a through hole. The connector assembly may further include a connector sized and configured to engage the through hole of one of the first and second flanges to fix the first and second portions relative to one another. A surface of one of the first and second flanges may include radial features configured to engage an opposing surface of the other of the first and second flanges to fix the first and second portions relative to one another.

In aspects of the present disclosure, the angle is defined about an axis orthogonal to the first and second axes and perpendicular to the sidewalls of the first and second portions.

In aspects of the present disclosure, the angle is defined about an axis orthogonal to the first and second axes and perpendicular to the top and bottom surfaces of the first and second portions.

In aspects of the present disclosure, a method for spinal surgery includes positioning a first portion of a multi-planar axial spinal rod connector over an end of a first spinal rod, positioning a second portion of the multi-planar spinal rod connector of an end of a second spinal rod, and fixing the first and second portions of the first and second spinal rods to the first and second spinal rods respectively. The first spinal rod defines a first axis and the second spinal rod defines a second axis. The method may include coupling the first and second portions in fixed relation to one another. In embodiments, coupling includes engaging a through hole of a flange of one of the first and second portions.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 1 is a perspective view of an exemplary embodiment of a multi-planar axial spinal rod connector in accordance with the present disclosure with first and second portions that are adjustable posteriorly or anteriorly relative to one another;

FIG. 2 is a longitudinal, side cross-sectional view of the rod connector of FIG. 1;

FIG. 3 is an exploded view of the rod connector of FIG. 1 showing the components thereof;

FIG. 7 is a perspective view of another exemplary embodiment of a multi-planar axial spinal rod connector in accordance with the present disclosure with first and second portions that are adjustable medially relative to one another;

FIG. 8 is an exploded view of the rod connector of FIG. 7 showing the components thereof;

FIG. 9 is a top view of the rod connector of FIG. 7;

DETAILED DESCRIPTION

Figure 4:
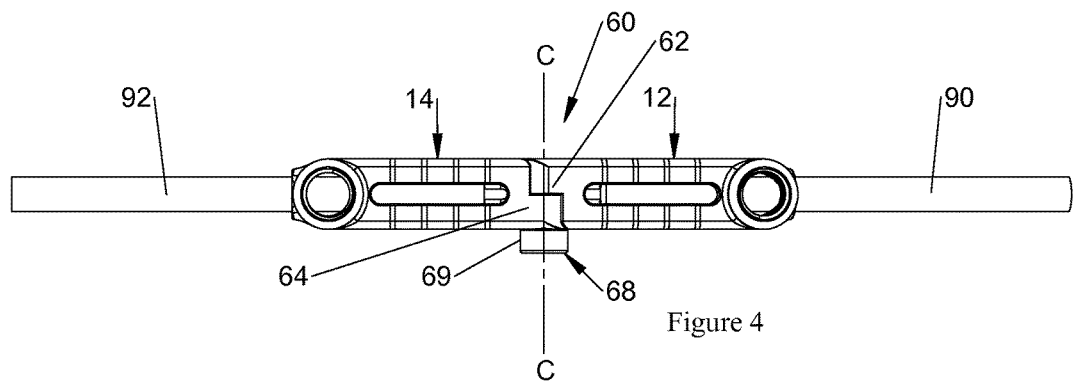
FIG. 4 is a top view of the rod connector of FIG. 1 with a spinal rod slidably received within the passage of each portion and the first and second portions articulatable with respect to one another.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "medial" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

With reference to FIGS. 1-3, a multi-planar axial spinal rod connector 10 is provided in accordance with the present disclosure including first and second portions 12, 14 joined by a connector assembly 60. First portion 12 defines an axis A-A and second portion 14 defines an axis B-B. First and second portions 12, 14 are similar to one another with like elements represented with like labels.

First and second portions 12, 14 have outer end portions 12a, 14a respectively. A passage 20 is defined about each of axes A-A, B-B extending from outer end portions 12a towards connector assembly 60. As shown, passages 20 are generally cylindrical. It is envisioned that passages 20 have shapes other than cylindrical. It is also envisioned that one passage 20 can have a first shape in the first portion 12 and the other passage 20 can have a second shape different from the first shape in the second portion 14. In some embodiments, passage 20 is stepped such that the portion of passage 20 adjacent connector assembly 60 has a diameter less than the diameter of the portion of passage 20 through outer end portions 12a, 14a of first and second portions 12, 14. The step of passage 20 forms a stop 22 near connector assembly 60. Stop 22 defines a gap 24 with connector assembly 60 as shown in FIG. 2. The gap is of sufficient size to receive a nub (not shown) of a pusher instrument (not shown) that is configured to adjust the length of a spinal rod within the passage 20. Such a pusher instrument is disclosed in co-owned and co-pending U.S. patent application Ser. No. 14/013,641, the content of which is incorporated in its entirety.

Outer end portions 12a, 14a each define a blind hole 30 extending through the top surface of first and second portions 12, 14 into passage 20 orthogonal to the respective axes A-A, B-B. Blind holes 30 include threads 31 that are configured to cooperate with threads 51 of set screws 50. Set screws 50 have sufficient length to engage threads 31 and interfere with passage 20. First and second portions 12 and 14 can each define a slot 40 between outer end portions 12a, 14a and connector assembly 60. Slot 40 extends through the top surface of each portion 12, 14 and into passage 20. In embodiments, slot 40 is a through-slot extending through the top and bottom surfaces of each of first and second portions 12, 14. The top surface of first and second portions 12, 14 can have markings 15 spaced at predefined distances along slot 40.

Connector assembly 60 defines an axis C-C that passes through first and second portions 12, 14 perpendicular to sidewalls thereof intersecting and orthogonal to axes A-A, B-B. Connector assembly 60 is configured to adjust first and second portions 12, 14 in a fixed plane relative to one another about axis C-C. First and second portions 12, 14 define an angle $\theta_1$ between axis A-A and axis B-B about axis C-C corresponding to posterior or anterior deflection of one of first and second portions 12, 14 relative to the other portion 12, 14. Each of first and second portions 12, 14 include a flange 62, 64 positioned at an inner end of first and second portions 12, 14, respectively. Each flange 62, 64 defines a through connecting hole 63, 65 sized and configured to receive a connector 68. A surface 62a of flange 62 can include radial features configured to engage a corresponding surface of flange 64 to fix first and second portions 12, 14 relative to one another. The corresponding surface of flange 64 may also include radial features configured to engage the radial features of surface 62a. The radial features may be teeth, splines, ribs, ridges, etc. configured to engage an opposing surface and/or radial features of the opposing surface to fix the position of the surfaces relative to one another. As shown in FIG. 3, connecting hole 63 is threaded and configured to cooperate with threads 68a of connector 68. Connecting hole 65 includes a recess 66 sized and configured to receive connector 68 such that a head 69 of connector 68 is flush with or disposed within the sidewall of second portion 14.

Figure 5:
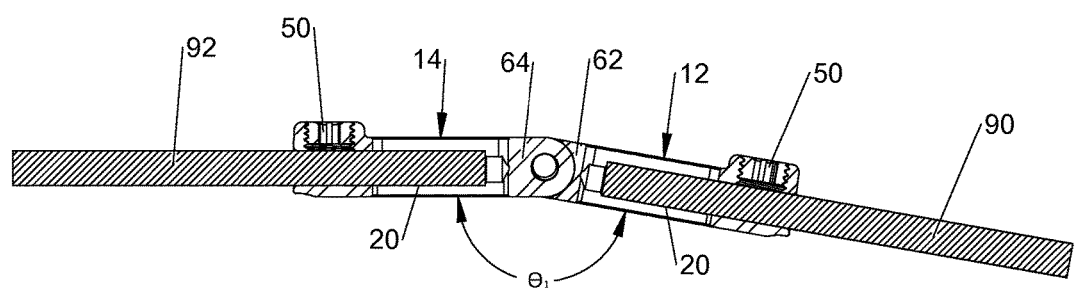
FIG. 5 is a longitudinal, side cross-sectional view of the rod connector and spinal rods shown in FIG. 4.
Figure 6:
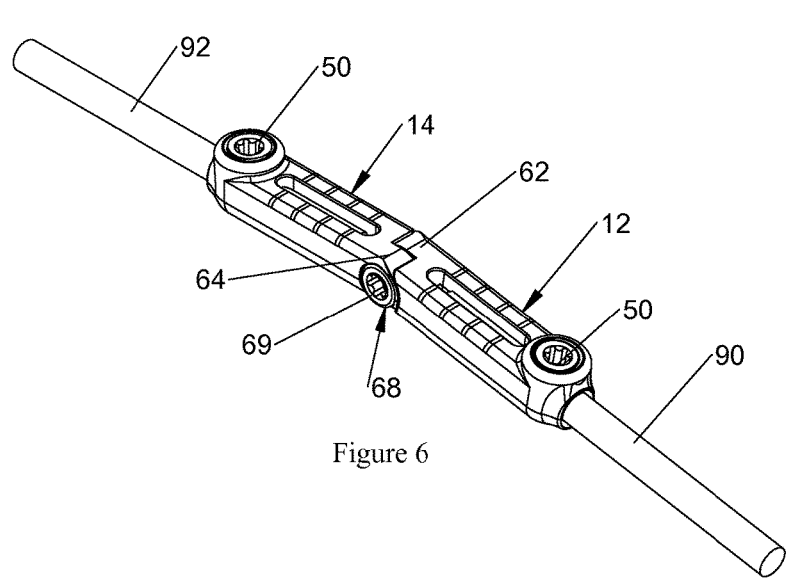
FIG. 6 is a perspective view of the rod connector of FIG. 1 with a spinal rod fixed in the passage of each of the first and second portions and the first and second portions fixed at an angle relative to one another.

Referring to FIGS. 4-6, during installation of rod connector 10, angle $\theta_1$, between axes A-A and B-B, is adjustable. Angle $\theta_1$ may be adjustable between about 45° to about 315°. In another embodiment, angle $\theta_1$ can be in a range of about 180° to about 90° or 270° depending on the relative rotation of the first and second portions 12, 14. In a further embodiment, angle $\theta_1$ can be in a range of about 170° to about 90°. It will be appreciated that during installation angle $\theta_1$ may initially be about 0° or 180° and is adjustable in either direction, i.e., clockwise or counter-clockwise about axis C-C. As shown in FIG. 4, connector 68 is in a first position such that first and second portions 12, 14 are adjustable with respect to one another about axis C-C. Passage 20 of first portion 12 is positioned over a first spinal rod 90 and passage 20 of second portion 14 is positioned over a second spinal rod 92 as shown in FIG. 5. Spinal rods 90, 92 are inserted a desired length thereof into passages 20 and fixed relative to first and second portions 12, 14 by set screws 50. Methods and a pusher instrument for axially fixing spinal rods at a desired length are disclosed in co-owned and co-pending U.S. patent application Ser. No. 14/013,641, the content of which is incorporated in its entirety. Head 69 of connector 68 is rotated to fix first and second portions 12, 14 relative to one another. The radial features of surfaces 62a and 64b (FIG. 2) of flanges 62, 64 may cooperate to fix first and second portions relative to one another. When first and second portions 12, 14 are fixed, head 69 of connector 68 is flush with or disposed within the sidewall of second portion 14 as shown in FIG. 6.

Referring to FIGS. 7-9, another multi-planar axial spinal rod connector 110 is provided in accordance with the present disclosure including a first portion 112, a second portion 114, and a connector assembly 160. First and second portions 112, 114 of rod connector 110 are similar to first and second portions 12, 14 of rod connector 10, as such only the differences will be discussed in detail below.

Connector assembly 160 defines an axis D-D that passes through first and second portions 112, 114 perpendicular to the top and bottom surfaces thereof intersecting and orthogonal to axes A-A, B-B. Connector assembly 160 is configured to adjust first and second portions 112, 114 in a fixed plane relative to one another about axis D-D. First and second portions 112, 114 define an angle $\theta_2$ between axis A-A and axis B-B about axis D-D corresponding to medial deflection of one of first and second portions 112, 114 relative to the other portion 112, 114. Angle $\theta_2$ may be adjustable between about 45° to about 315°. It will be appreciated that during installation angle $\theta_2$ may initially be about 0° or 180° and is adjustable in either direction, i.e., clockwise or counter-clockwise about axis D-D. In another embodiment, angle $\theta_2$ can be in a range of about 180° to about 90° or 270° depending on the relative rotation of the first and second portions 112, 114. In a further embodiment, angle $\theta_2$ can be in a range of about 170° to about 90°. Each of first and second portions 112, 114 includes a flange 162, 164 positioned at an inner end of first and second portions 112, 114, respectively. Each flange 162, 164 defines a through connecting hole 163, 165 sized and configured to receive a connector 168. A surface 162a of flange 162 can include radial features configured to engage a corresponding surface of flange 164 to fix first and second portions 112, 114 relative to one another. The corresponding surface of flange 164 may also include radial features configured to engage the radial features of surface 162a. As shown in FIG. 8, connecting hole 163 is threaded and configured to cooperate with threads 168a of connector 168. Connecting hole 165 includes a recess 166 sized and configured to receive connector 168 such that a head 169 of connector 168 is flush with or disposed within the top surface of second portion 114. The use of rod connector 110 is substantially similar to the use of rod connector 10 described above.

Figure 10:
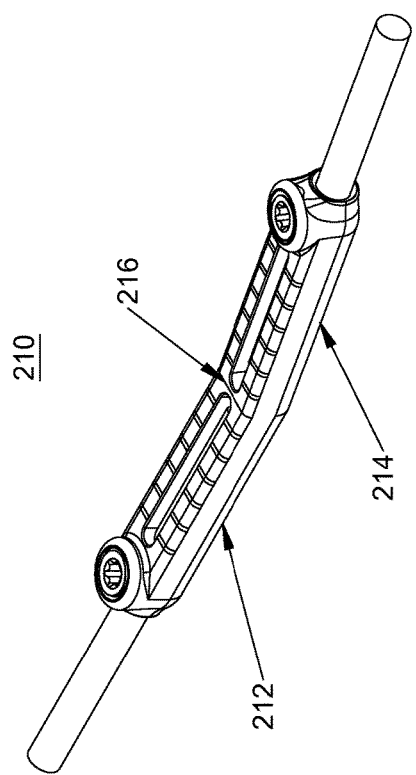
FIG. 10 is a perspective view of yet another exemplary embodiment of a multi-planar axial spinal rod connector in accordance with the present disclosure with first and second portions that define a fixed angle posteriorly or anteriorly relative to one another.
Figure 11:
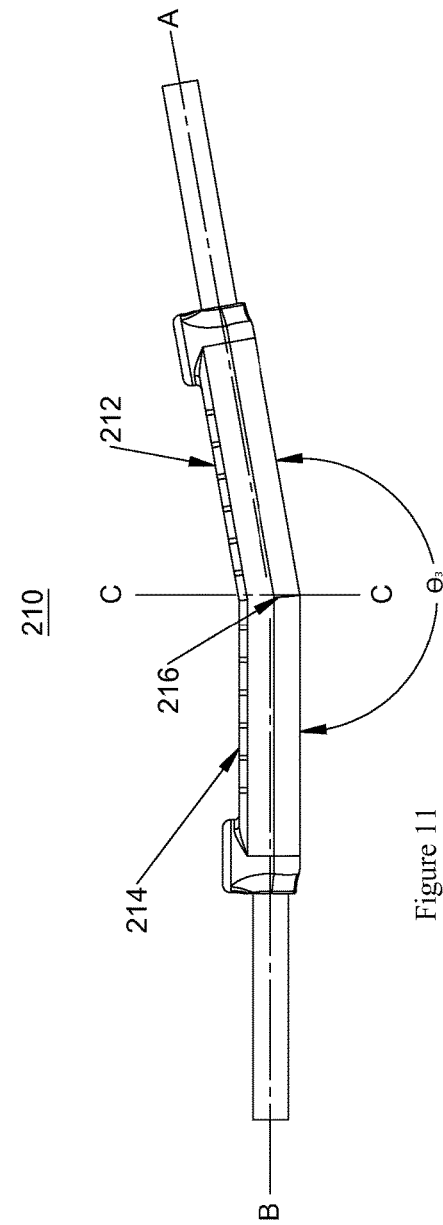
FIG. 11 is a side view of the rod connector of FIG. 10.
Figure 12:
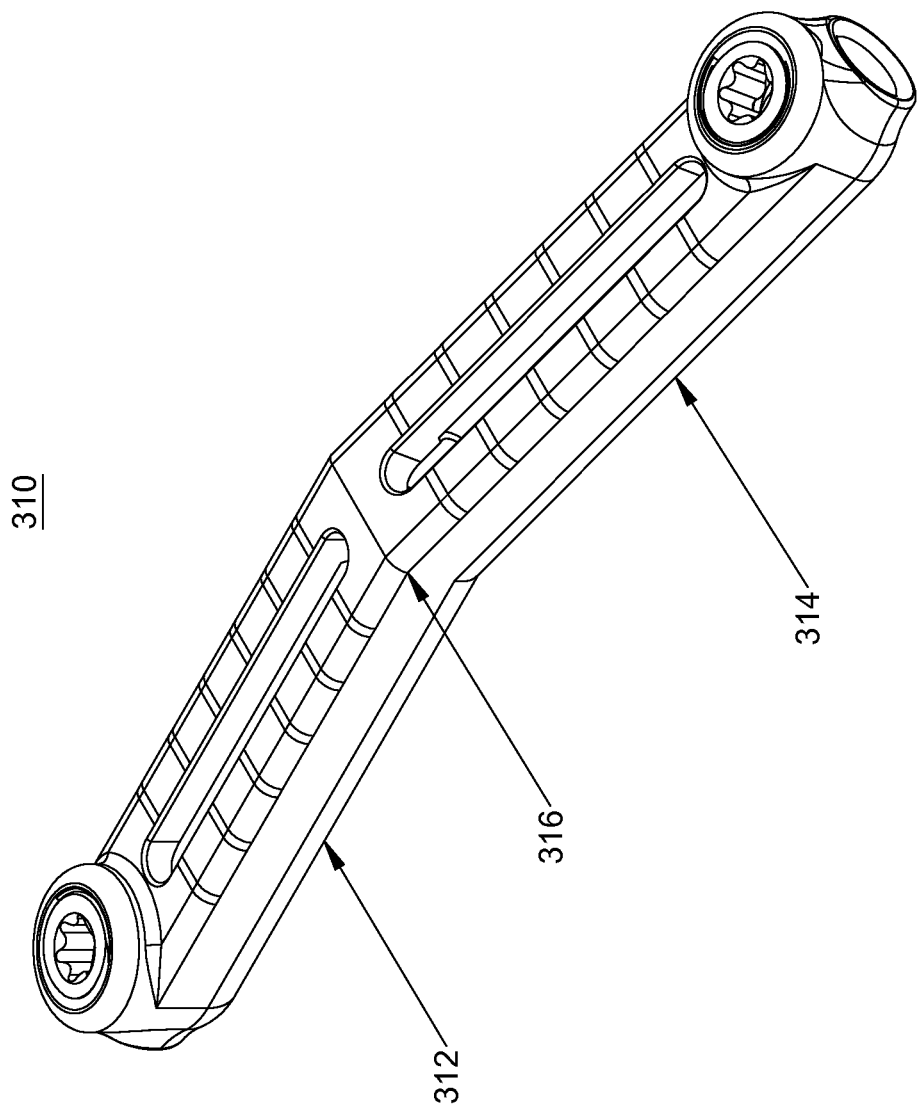
FIG. 12 is a perspective view of still yet another exemplary embodiment of a multi-planar axial spinal rod connector in accordance with the present disclosure with first and second portions that define a fixed angle posteriorly or anteriorly relative to one another.

Referring to FIGS. 10 and 11, yet another multi-planar axial spinal rod connector 210 is provided in accordance with the present disclosure including a first portion 212 and a second portion 214 integrally joined at an angled connector 216. First and second portions 212, 214 of rod connector 210 are similar to first and second portions 12, 14 of rod connector 10, as such only the differences will be discussed in detail below.

With particular reference to FIG. 11, angled connector 216 defines a predefined angle $\theta_3$ between axis A-A and axis B-B about axis C-C corresponding to posterior or anterior deflection of one of first and second portions 212, 214 relative to the other portion 212, 214. Angle $\theta_3$ may be in a range of about 45° to about 315°.

In aspects of the present disclosure, any or all of the screws, e.g., screws 50, 68, 150, and 168, further include one or more locking mechanisms configured such that, when the screw is inserted into hole, the locking mechanism maintains the screw within the hole. The locking mechanism may include, for example, a locking ring positionable in the hole for retaining the screw, a lip formed in the hole with the screw made of a harder material than the hole such that a thread on the screw, e.g., a second screw thread disposed about the screw head, locks to the lip upon engagement of the screw with the lip, or any other suitable locking mechanism.

In aspects of the present disclosure, the multi-planar axial spinal rod connectors described above may be constructed of a variety of biocompatible materials, e.g., stainless steel, cobalt chrome, PEEK, titanium, titanium alloys, etc.

In aspects of the present disclosure, the spinal rods described above may be made in various diameters and various shapes and may be constructed of a variety of biocompatible materials, e.g., stainless steel, cobalt chrome, PEEK, titanium, titanium alloys, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A multi-planar axial spinal rod connector comprising:
    a first portion defining a first longitudinal axis and defining a first passage coaxial with the first longitudinal axis sized and configured to slidably receive a portion of a first spinal rod therein, the first portion having top and bottom planes and defining a first slot through the top plane, the first slot defining a first longitudinal slot axis parallel to the first longitudinal axis;
    a second portion defining a second longitudinal axis different from the first longitudinal axis and defining a second passage coaxial with the second longitudinal axis sized and configured to slidably receive a portion of a second spinal rod therein; and
    a connector assembly including a connector having a central longitudinal axis coaxial with a pivot axis that is orthogonal to and passes through the first and second longitudinal axes, the connector rotatable relative to the first and second portions and configured to fix the first and second portions in fixed relation to one another such that the first and second longitudinal axes define an angle relative to one another about the pivot axis, the pivot axis orthogonal to the first and second longitudinal axes and orthogonal to the top and bottom planes of the first portion.

2. The spinal rod connector of claim 1, wherein the connector assembly integrally is formed with the first and second portions.

3. The spinal rod connector of claim 1, wherein the angle is adjustable.

4. The spinal rod connector of claim 3, wherein the angle is in a range of about 45° to about 315°.

5. The spinal rod connector of claim 3, wherein the first portion includes a first flange and the second portion includes a second flange, the first and second flanges each defining a through hole about the pivot axis.

6. The spinal rod connector of claim 5, wherein the connector is sized and configured to engage the through hole of at least one of the first and second flanges to fix the first and second portions relative to one another.

7. The spinal rod connector of claim 5, wherein a surface of at least one of the first and second flanges includes radial features, the radial features configured to engage an opposing surface of the other of the first and second flanges to fix the first and second portions relative to one another.

8. The spinal rod connector of claim 1, wherein the first portion defines a blind hole, the blind hole formed about a hole axis that is orthogonal to the first longitudinal axis and the first longitudinal slot axis.

9. The spinal rod connector of claim 8, further comprising a set screw that is threadably inserted into the blind hole, the set screw configured to secure a rod within the first passage.

10. A method for spinal surgery, comprising:
positioning a first portion of a multi-planar axial spinal connector over an end of a first spinal rod parallel to a longitudinal axis of a spine of a patient, the first spinal rod defining a first longitudinal axis parallel to a longitudinal axis of the first portion and having a constant diameter;
positioning a second portion of the multi-planar axial spinal connector over an end of a second spinal rod, the second spinal rod defining a second longitudinal axis different from the first longitudinal axis;
fixing the first and second portions to the first and second spinal rods respectively such that the first and second portions are medially deflected relative to one another; and
tightening a connector to secure the first and second portions in fixed relation to one another such that the first and second longitudinal axes define an angle relative to one another about a pivot axis, the connector disposed orthogonal to the first and second longitudinal axes and defining a central longitudinal axis coaxial with the pivot axis.

11. The method of claim 10, wherein tightening a connector to secure the first and second portions in fixed relation to one another includes the connector engaging a through hole of a flange of at least one of the first and second portions.

12. A multi-planar axial spinal rod connector comprising:
a first portion defining a first unthreaded blind hole configured to slidably receive a portion of a first spinal rod, the first portion defining a first screw hole along a first screw axis;
a second portion defining a second blind hole configured to slidably receive a portion of a second spinal rod, the second portion defining a second screw hole along a second screw axis parallel to the first screw axis; and
a connector assembly coupling the first portion to the second portion such that one of the first and second portions is pivotable with respect to the other of the first and second portions about a pivot axis, thereby defining an angle therebetween, the connector assembly including a connector having a central longitudinal axis coaxial with the pivot axis, the connector rotatable relative to the first and second portions and configured to secure the first and second portions in fixed relation to one another about the pivot axis, the pivot axis parallel to the first and second screw axes.

13. The spinal rod connector according to claim 12, wherein at least one position of connector assembly aligns the first spinal rod with the second spinal rod.

14. The spinal rod connector according to claim 12, wherein the first portion includes a first set screw configured to interfere with the first blind hole.

15. The spinal rod connector according to claim 14, wherein the first set screw has a first position wherein the portion of the first spinal rod received within the first blind hole is slidable relative to the first portion and a second position wherein the portion of the of the first spinal rod received within the first blind hole is fixed relative to the first portion.

16. The spinal rod connector according to claim 12, wherein the second portion includes a second set screw configured to interfere with the second blind hole.

17. The spinal rod connector according to claim 16, wherein the second set screw has a first position wherein the portion of the second spinal rod received within the second blind hole is slidable relative to the second portion and a second position wherein the portion of the of the second spinal rod received within the second blind hole is fixed relative to the second portion.

* * * * *